United States Patent [19]

Ehrgott

[11] Patent Number: 4,495,798

[45] Date of Patent: Jan. 29, 1985

[54] METHOD AND APPARATUS FOR MEASURING CONSISTENCY OF NON-NEWTONIAN FLUIDS

[75] Inventor: Charles W. Ehrgott, Madison, Conn.

[73] Assignee: Chesebrough-Pond's Inc., Greenwich, Conn.

[21] Appl. No.: 451,672

[22] Filed: Dec. 21, 1982

[51] Int. Cl.³ .............................................. G01N 11/02
[52] U.S. Cl. ........................................ 73/54; 73/61 R; 73/169
[58] Field of Search .................... 73/55, 61 R, 169, 56, 73/54, 861.04

[56] References Cited

U.S. PATENT DOCUMENTS

| | | | |
|---|---|---|---|
| 2,459,438 | 1/1949 | Zimmer et al. | 73/55 |
| 2,673,463 | 3/1954 | Kimball et al. | 73/169 X |
| 2,834,200 | 5/1958 | Rhodes et al. | 73/55 |
| 2,896,656 | 7/1959 | Allen et al. | 73/56 |
| 2,934,944 | 5/1960 | Eolkin | 73/55 |
| 3,024,643 | 3/1962 | Jones, Jr. | 73/55 |
| 3,116,630 | 1/1964 | Piros | 73/55 |
| 3,435,665 | 4/1969 | Tzentis | 73/56 |
| 3,548,638 | 12/1970 | Uchida et al. | 73/55 |
| 3,677,069 | 7/1972 | Rubin et al. | 73/56 |
| 3,952,577 | 4/1976 | Hayes et al. | 73/55 |
| 4,258,564 | 3/1981 | Humlme et al. | 73/61 R |

FOREIGN PATENT DOCUMENTS 1005607  9/1965  United Kingdom ............... 73/55

Primary Examiner—Gerald Goldberg
Assistant Examiner—Hezron Williams
Attorney, Agent, or Firm—Millen & White

[57] ABSTRACT

A method and device for determining the consistency of a non-Newtonian fluid in accordance with USDA Bostwick consistency standards comprises diverting a partial stream from a main production stream of the fluid. The flowrate of this partial stream in weight per time is measured under predetermined pressure drop conditions. The USDA Bostwick value of consistency is then derived from the measured flowrate in accordance with a predetermined functional relationship.

15 Claims, 4 Drawing Figures

METHOD AND APPARATUS FOR MEASURING CONSISTENCY OF NON-NEWTONIAN FLUIDS

BACKGROUND OF THE INVENTION

This invention relates to a method and device for determining USDA Bostwick consistency values of a non-Newtonian fluid, and more particularly, for determining the consistency of a thick material such as tomato paste, directly from a material production stream without conducting presently complicated required USDA procedures for determining USDA Bostwick consistency values.

Consistometers such as the Bostwick consistometer developed by E. P. Bostwick of the USDA in 1938, and given official status for use in consistency grading of puréed products such as tomato catsup were developed to establish a fixed set of values for grading these products according to the subjective quality known as consistency. Another consistometer developed for measuring the consistency of such purées is the modified Adams consistometer. Typically, both the Bostwick and the Adams consistometer are very simple devices which measure the amount of slump or flattening out of a purée over a predetermined time interval. The derivation of mathematical equations describing Bostwick consistometer performance is difficult, yet it has found wide application in the food industry because of its ease of operation and good correlation with consistency as the consumer subjectively senses this property. However, these devices are only good for batch measurements and highly inadequate in continuous processes.

It has been proposed as an alternative to employ one of many well built and mathematically calculable viscosimeters to determine consistency as a method of adaptation to continuous processes. However, laboratory tests have shown that viscosimeters do not measure the same properties as does the Bostwick device, and in fact, the Bostwick device does a much better job in indicating actual consumer preferances.

The problem with using a viscosimeter to measure consistency is that each measurements treat a purée as if it is a true liquid, with the viscosity being measured at a single selected shear rate. This approach requires two assumptions. First, that one deals with a true normal liquid and, second, that the first assumption is probably in error but that there is sufficient proportionality between the measured and real properties to make the measurements of value. Since the proportionality is not constant, and in some cases varies greatly, the resulting measurements can be highly misleading.

Another attempt to solve the problem of consistency measurements of continuous flows is discussed in the article entitled, *The Plastometer—A New Development in Continuous Recording and Controlling Consistometers* by David Eolkin, Food Technology Journal, Jan. 11, 1952. This article discusses a device which branches-off a partial flow from a product line into a dual bridge and causes pressure drop differences to arise by varying respective tube diameters. These measurements are then employed to measure the structure of the component product. On the other hand, as discussed in page 256 of the article, the true consistometer does not distinguish between the consistency and viscosity but measures the system as a whole. Thus, in some instances the resulting measurements from the plastometer will be quite different from actual consistency values. Further, in no way does this device attempt to correlate measurements with USDA Bostwick.

SUMMARY OF THE INVENTION

It is thus an object of the present invention to provide a method of measuring consistency of a continuous production stream of a non-Newtonian fluid, such as a purée.

Another object of the invention is to provide a device for measuring the consistency of a stream of a non-Newtonian fluid at selected times.

Still another object of the invention is to provide a method and device for measuring the consistency of a continuous production stream of a foodstuff such as tomato paste.

Upon further study of the specification and appended claims, further objects and advantages of this invention will become apparent to those skilled in the art.

In accordance with the method of the invention, the flowrate of a continuous stream of a non-Newtonian fluid is measured at a known temperature and known pressure drop. The USDA Bostwick value of consistency of the fluid is then determined by correlation of the measured flowrate at the known temperature and, pressure drop in accordance with a predetermined functional relationship to provide a predictive value indicative of the USDA Bostwick value of consistency of the material. In another aspect, the invention comprises conducting said measurements on a partial stream branched-off from a continuous production stream.

In order to practice the method, a device is arranged associated with a conduit through which the continuous stream of the non-Newtonian fluid flows. Diverting means are provided. Typically a smaller diameter conduit with a valve, is in communication with the above-discussed conduit, and adapted for periodically diverting a partial stream of the non-Newtonian fluid therethrough. Means are provided for measuring the temperature, and measuring and regulating pressure drop of the diverted partial stream of fluid, and measuring means for simultaneously measuring the flowrate of the partial stream is associated therewith whereby values measured by said assembly of means can be correlated in a predetermined functional relationship to obtain a predictive value indicative of the actual USDA Bostwick value of consistency of the continuous stream of the non-Newtonian fluid flowing through the conduit.

DETAILED DISCUSSION OF THE INVENTION

Figure 1:
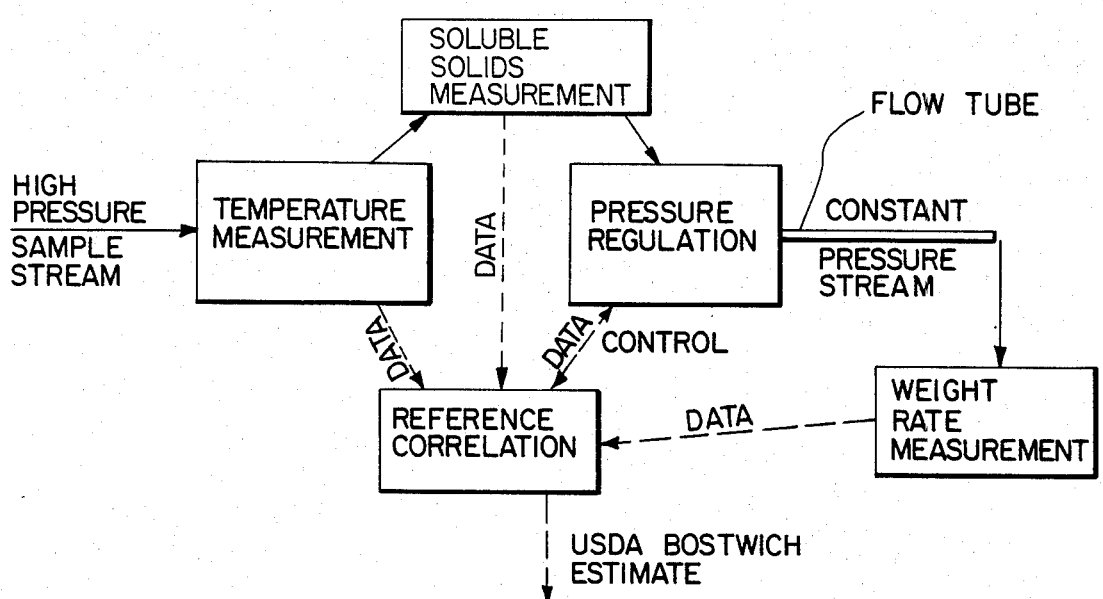
FIG. 1 is a block diagram generally illustrating the method of conducting the method of the invention.

A block diagram is illustrated in FIG. 1 showing generally how to conduct the method of the invention whereby a continual estimate of consistency in accordance with the USDA Bostwick value scale can be predicted for a non-Newtonian fluid, i.e., a paste, being produced in a continuous stream.

The method requires that the temperature of a sample or partial stream be measured and the pressure regulated to a selected pressure drop value, with the flowrate of the material, i.e., the paste, measured in weight per time through a predetermined flow-tube system, i.e., one of predetermined length and diameter.

Figure 2:
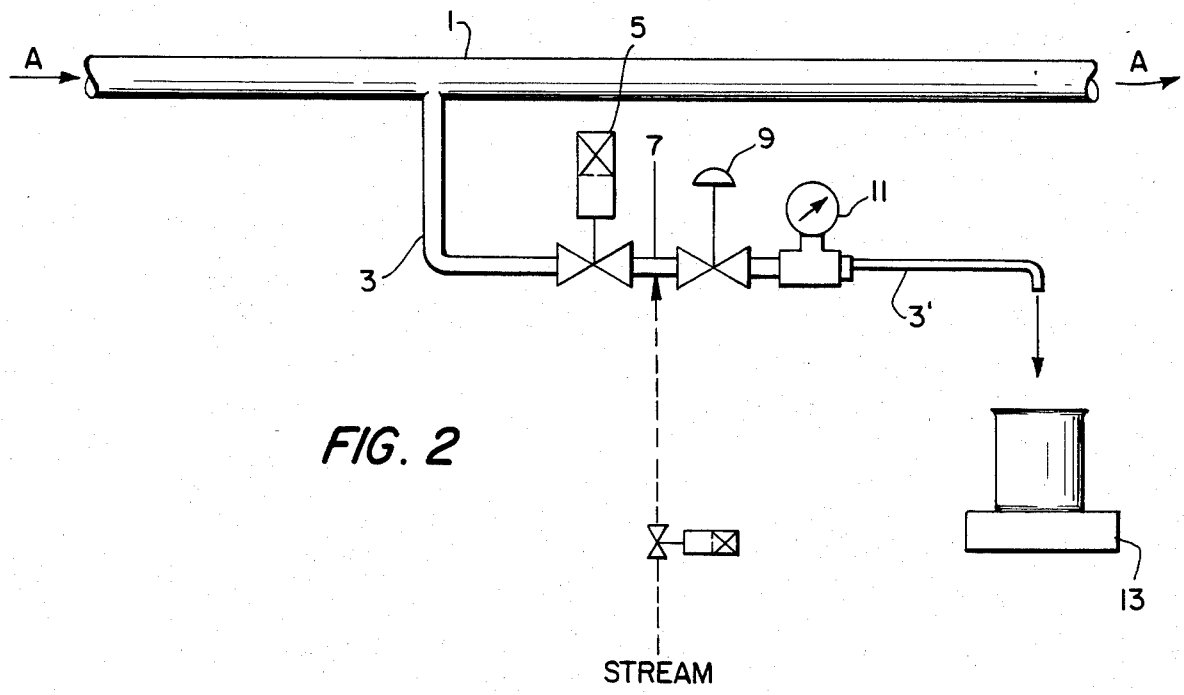
FIG. 2 is a schematic diagram of one embodiment of a device for conducting the method of the invention.

One embodiment of an apparatus for carrying out the process of the invention is illustrated in FIG. 2. More particularly, this figure illustrates a main pipeline 1 connected to a source of paste production wherefrom pumps force the material through the pipeline 1 to a filling station in the direction of the arrows A.

A branch flow line 3 is connected to the main pipeline 1 for diverting a partial flow of the paste from the main flow. The diverting of the partial flow is controlled by an aseptic valve 5 so that periodic measurements of flowrate can be made in a predetermined manner to determine the consistency of the main production stream. The temperature of the partial stream is measured by a temperature measuring means located at 7, such as a Wahl pyrometer (not shown), associated downstream from the valve 5 with pressure regulation means 9 provided associated with a pressure gauge 11 for measuring and regulating the pressure drop of the partial stream to a pre-selected value. The valve 5 can be any type of quick-open/quick-close valve such as a plug cock, stem and seat, or ball valve meant to rapidly divert the production stream. By aseptic valve is meant anyone of these valves with the additional features of stem seals at any point where bacteria would enter the system. Basically, what is important is that standard aseptic practice be complied with. One such aseptic valve useful in the device is known by those skilled in the art as an APC Air Operated Stainless Steel Sanitary Aseptic Valve manufactured by Alloy Products Corp.

The partial stream then flows out of the branch flow line 3 through a smaller diameter section 3', of at least $\frac{1}{4}''$ in diameter and about 2 feet in length, and onto a balance. Other tube diameters which can be employed include $\frac{3}{8}''$ and $\frac{1}{2}''$, which perform similar to the $\frac{1}{4}''$ tube. However, it is desirable to use the smallest diameter tube to ensure that only small amounts of paste are wasted. The rate of flow in weight/time onto the balance is measured in a conventional manner. The values of flowrate, pressure drop and temperature are then correlated in a predetermined functional manner. This system is especially adapted for manual operation by an operator. However, it is just as easy for those skilled in the art to modify such a system, in a conventional manner, for automatic operation at preselected intervals to maintain strict quality controls on material production. Moreover, an alarm system can be provided with this system which is actuable whenever the consistency value of the production stream exceeds certain limits. All of these modifications would be well known to those skilled in the art.

Figure 3:
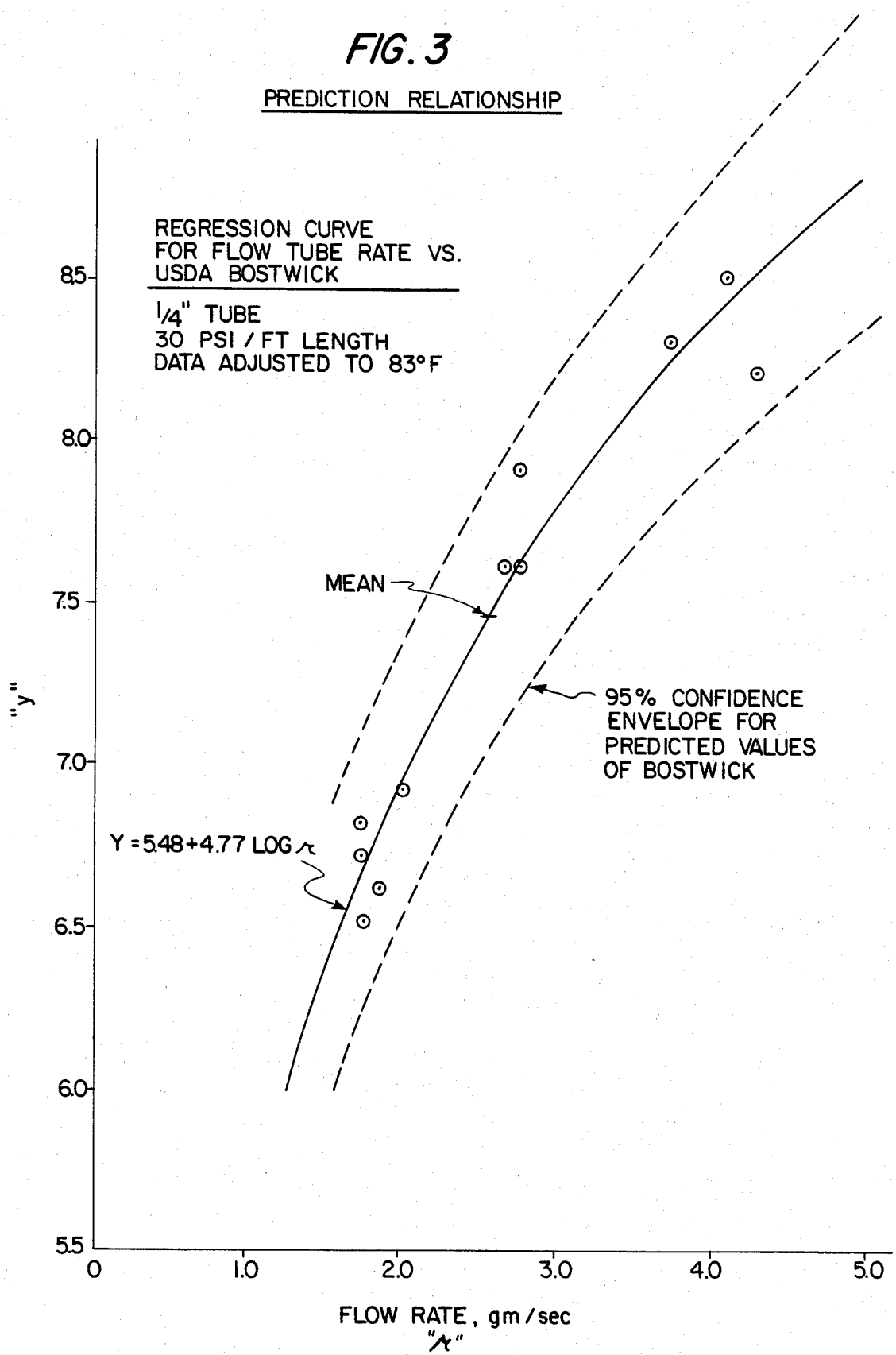
FIG. 3 is a graph illustrating the relationship between Bostwick values and measured values of flow rate obtained according to the method of the invention.

The method according to the invention relies on the fact that the USDA Bostwick consistency value of the paste can be calculated in accordance with the following functional relationship:

$$y = 5.38 + 4.77 \log r$$

wherein y is the predicted USDA Bostwick value obtained by conducting the method of the invention, and r is the measured flow rate in grams/sec. This relationship was derived from experimental work as discussed hereinafter. A more general relationship would be $$y = a + b \log r$$

wherein a and b are constants, and r is the measured flowrate in grams/sec. The constants a and b are developed by the user for any individual process because processing conditions, will to some degree, affect USDA Bostwick values. If the paste flowrate is known, then the actual USDA Bostwick value should 95% of the time lie within the confidence envelope as shown in FIG. 3. This is specific only for the data set forth in the examples set forth hereinafter, but exemplifies the prediction accuracy of the method.

In one embodiment, this method is conducted through a $\frac{1}{4}''$ tube of about 2 feet in length at a pressure drop of 30 psi/foot length at a temperature of 83° F. If the temperature varies from 83° F., a correction, which is to be added to or subtracted from the measured flowrate, i.e., subtracted if the temperature is higher and added if the temperature is lower, is determined in accordance with the following functional relationship for temperature:

$$C = \text{correction factor } 0.4 \text{ gm/sec}/F.° \times F.°$$

wherein C is the correction to be added or subtracted. Thus, for example a flowrate of 1.45 gm/sec measured at 76° F. would require a correction equal to $(83-76) \times 0.04$ or more specifically, a correction of +0.28 gm/sec. Thus, the corrected flowrate would equal 1.73 gm/sec.

Although not affecting flowrate values as much as temperature, the amount of solids in the material also affects the flowrate. This amount of solids is conventionally measured as the °Brix solids factor; which is well known to those skilled in the art as generally indicating the percentage of soluble solids in the material. This °Brix factor is not a precise measure of the soluble solids, but nonetheless, it is a fairly accurate and conventionally used representation.

In the method of the invention, for the most accurate prediction of the USDA Bostwick consistency value from the obtained flowrate measurement, the measurements should be conducted on a paste having a °Brix factor of 31.6. If the °Brix solids value is different from said value, a correction to the measured flowrate can be applied by multiplication by a correction factor of A/31.6 wherein A is the actual °Brix solids value of the paste being measured. Thus, for example, for a paste flowrate of 1.78 gm/sec at a temperature of 83° F. and having a °Brix value factor of 31.9, the measured flowrate would be multiplied by 31.9/31.6 to obtain the corrected flowrate employed in order to obtain the Bostwick values, i.e., the corrected flowrate would be 1.80. Nonetheless, even if the °Brix factor correction is not applied, the calculated Bostwick value would still fall within the previously discussed 95% confidence range. However, by applying the °Brix value factor correction a more accurate estimate of the USDA Bostwick value of consistency can be obtained. Nonetheless, application of a °Brix correction factor would generally be impractical. Thus, it is best to monitor °Brix solids at a point upstream, and by careful control of processing conditions from that point on, a °Brix control of $N \pm 1\%$ can be maintained. Furthermore, it should be noted that when making corrections for differences in temperature and solids, that temperature corrections should be made first and the corrections for solids should be made on the temperature corrected value. Moreover, corrections for variances in amounts of solids need not be a factor, and can be eliminated as a factor by merely maintain strict quality controls with respect to suspended solids during production.

Without further elaboration, it is believed that one skilled in the art can, using the preceding description utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Farenheit; unless otherwise indicated, all parts and percentages are by weight.

EXAMPLES

Test Apparatus and Use Thereof In Testing

Figure 4:
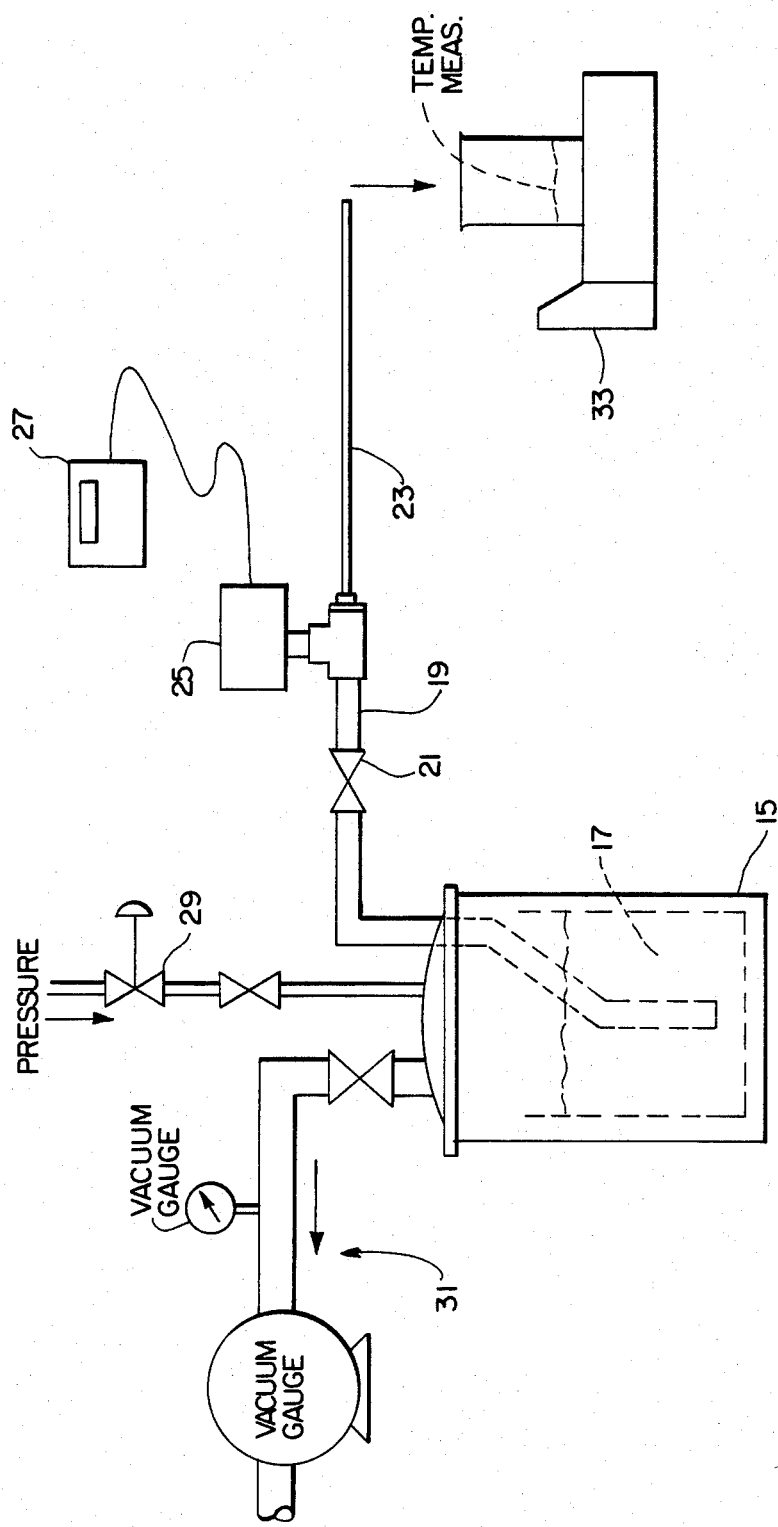
FIG. 4 is a schematic diagram illustrating an experimental apparatus employed in testing the operability of the method of the invention.

In conducting tests for determining the feasibility of the method, an experimental apparatus, as shown in FIG. 4, was employed.

More specifically, a sample of paste, about 4 gallons, was loaded into a pressure pot 15 which was sealed. A moderate vacuum, i.e., about 26-27″ Hg, was drawn through a vacuum pumping system 31 to promote degassing from paste interstices without loss of water. After a settling period sufficient to eliminate voids in the paste caused by degassing, runs were begun by closing the vacuum valve, then opening air pressure valve 29 and discharge valve 21 to cause the paste to flow into and through discharge tube 19. An electronic pressure gauge 25, typically a Heiss electronic gauge, was employed to maintain a predetermined pressure value whereby the paste was passed through a ¼″ diameter flow tube of approximately 2 feet in length at a pressure drop of 30 psi/ft. The rate of flow in gms/sec of the paste was measured by a laboratory balance 33 which was accurate to 0.01 gms and the temperature of the paste was measured in the balance 33 by conventional temperature measuring means (not shown).

Paste Samples Tested

Various samples of tomato paste were employed for these tests. A total of eleven samples were run with the samples designated in three groups, A, B and C, and with Group A being a thicker paste ranging in Bostwick values of 5.5-6.5, Group B ranging in values of 6.6-7.5, and Group C being the thinnest and ranging in values of 7.6-8.5. The runs were broken down into five A samples, three B samples and three C samples. Prior to testing, the USDA Bostwick consistency value for each sample was determined.

Before testing, the paste samples had been collected over a period of time as paste drums were opened for other purposes. These samples were kept refrigerated until the day befoe use, at which time they were placed in an environmental chamber, well known to those skilled in the art as a chamber wherein temperature and humidity conditions can be adjusted to desired values, and held overnight at 95° F.

During testing, two of the paste samples were run at a constant 30 psi/ft pressure drop at temperatures from about 55° F. to 85° F. and it was determined that a flow rate change of about 0.04 gm/sec occurs per degree Farenheit. From the data, it was determined that ideal testing conditions are at 83° F. with a ¼″ diameter tube of about 2 feet in length, at a pressure drop of 30 psi/ft. Values obtained at different temperatures were corrected as discussed above.

It was also discovered that the amount of solids also had a slight effect on the flowrate. The solids were measured as °Brix solids, with a solids amount of 31.6 °Brix being ideal. Thus, the measured flowrate was also corrected for any variance in solids from the 31.6 °Brix value. The results are illustrated in the following table:

TABLE
FLOW RATE ADJUSTMENTS

| Paste Grade (from drum) | USDA Bost. (Shelton) | Flow Rate gm/sec | NTSS (°Brix) | Temp. | Flow Rate w/temp correction $\left(\dfrac{0.04 \text{ gm/sec}}{\text{°F.}}\right)$ 83° F. = zero corr. | Flow Rate w/temp. and solids corr. (linear avg. solids = 31.6 °Brix) Correction Factor | |
|---|---|---|---|---|---|---|---|
| A | 6.5 | 1.78 | 31.9 | 83 | 1.78 | 31.9/31.6 | 1.80 |
| A | 6.6 | 1.92 | 31.1 | 84 | 1.88 | 31.1/31.6 | 1.85 |
| A | 6.7 | 1.82 | 30.9 | 84 | 1.78 | 30.9/31.6 | 1.74 |
| A | 6.8 | 1.45 | 31.1 | 76 | 1.73 | 31.1/31.6 | 1.70 |
| A | 6.9 | 2.02 | 30.9 | 83 | 2.02 | 30.9/31.6 | 1.97 |
| B | 7.6 | 2.72 | 32.4 | 84 | 2.68 | 32.4/31.6 | 2.75 |
| B | 7.9 | 2.82 | 31.6 | 84 | 2.78 | 31.6/31.6 | 2.78 |
| B | 8.3 | 3.76 | 31.8 | 83 | 3.76 | 31.8/31.6 | 3.78 |
| C | 7.6 | 2.82 | 32.3 | 84 | 2.78 | 32.3/31.6 | 2.84 |
| C | 8.2 | 4.44 | 31.7 | 86 | 4.32 | 31.7/31.6 | 4.33 |
| C | 8.5 | 4.13 | 31.5 | 83 | 4.13 | 31.5/31.6 | 4.12 |

The results of the testing were plotted on a graph, FIG. 3, resulting in an exponential curve which is indicative of the relationship between USDA Bostwick consistency and the corrected measured flowrates and as discussed previously, can be defined by specific functional relationship. Also graphed with the curve is the confidence envelope, i.e., 95% for predicted values of USDA Bostwick. In this regard, it is noted that the confidence range predicting USDA Bostwick consistency values from paste flow rates is considerably wider than one based strictly on a correlation of the results discussed above. This is because it includes a probabilistic variance, determined in a conventional manner to account for different data groups.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of measuring USDA Bostwick value consistency of a continuous production stream of tomato paste containing soluble, solids, the method comprising the steps of: establishing and maintaining a stream of said tomato paste; diverting a partial stream of said paste into a second stream thereof; regulating the flow of said paste in the second stream to achieve a predetermined pressure drop; measuring the weight flow rate of said paste in said second stream at the predetermined pressure drop; measuring the temperature of the partial stream and making a correction on the measured weight flow rate by a predetermined factor when the measured temperature differs from a predetermined temperature value; measuring the soluble solids content of said tomato paste partial stream and making a correction on the measured weight flow rate by predetermined factor when the measured amount of soluble solids differs from a predetermined soluble solids value; and correlating, in a predetermined functional relationship the said measured weight flow rate, to obtain the USDA Bostwick consistency value of the paste flowing in said established stream.

2. A method according to claim 1 wherein said measurement is conducted by passing the partial stream through a $\frac{1}{4}''$ diameter tube of about 2 feet in length, and at a pressure drop of 30 psi/ft.

3. A method according to claim 1, wherein said method is conducted at predetermined intervals on an automatic basis.

4. A method of measuring consistency of a continuous production stream of a non-Newtonian fluid comprising the steps of establishing and maintaining a stream of said fluid; regulating the flow of said fluid in the stream to achieve a predetermined pressure drop; measuring the weight flowrate of said fluid in said stream at the predetermined pressure drop; measuring the temperature of the stream and making a correction on the measured weight flowrate by a predetermined factor when the measured temperature differs from a predetermined temperature value; measuring the amount of soluble solids of said fluid stream and making a correction on the measured weight flowrate by a predetermined factor when the measured amount of soluble solids differs from a predetermined solids value; and correlating, in a predetermined functional relationship the said measured or corrected weight flowrate, to obtain the USDA Bostwick consistency value of the fluid flowing in said stream.

5. A method according to claim 4, further comprising controlling the amount of soluble solids of said fluid stream to fall within a predetermined range, then measuring the amount of soluble solids and making a correction on the measured flowrate by a predetermined factor when the measured amount of soluble solids differs from said predetermined soluble solids value.

6. A method according to claim 4 wherein said measurement is conducted by passing the stream through a $\frac{1}{4}''$ diameter tube of about 2 feet in length at a pressure drop of 30 psi/ft.

7. A method according to claim 4, wherein correlation of flowrate into Bostwick value is conducted with said known pressure drop at 30 psi/ft with the stream conducted through a $\frac{1}{4}''$ tube of about 2 feet in length, at a temperature of 83° F., and having an amount of soluble solids corresponding to a value of 31.6 °Brix, and wherein the Bostwick value is determined from the measured weight flowrate in accordance with a functional relationship of $$y = 5.48 + 4.77 \log r$$

wherein y is equal to the predicted Bostwick value and r is the measured flowrate with the correction factor applied.

8. A method according to claim 4, wherein said measurements are conducted on a stream of tomato paste.

9. A method according to claim 4, wherein said method is conducted at predetermined intervals on an automatic basis.

10. A method according to claim 4 further comprising diverting a partial stream from said established and maintained continuous production stream and conducting said process with said partial stream.

11. A method of measuring consistency of a continuous production stream of a non-Newtonian fluid comprising the steps of establishing and maintaining a stream of said fluid; regulating the flow of said fluid in the stream to achieve a predetermined pressure drop; measuring the weight flowrate of said fluid in said stream at the predetermined pressure drop; and correlating the measured weight flowrate to obtain the USDA Bostwick consistency value of the fluid in said stream by conducting the measurements with a known pressure drop of 30 psi/ft with the stream conducted through a $\frac{1}{4}''$ tube of about 2 feet in length, at a temperature of 83° F. and having an amount of soluble solids corresponding to a value of 31.6 °Brix, and wherein the Bostwick value is determined from the measured flowrate in accordance with a functional relationship of $$y = 5.48 + 4.77 \log r$$

wherein y is equal to the predicted Bostwick value and r is the measured weight flowrate with the correction factor applied.

12. A method according to claim 11, wherein said measurements are conducted on a stream of tomato paste.

13. A method according to claim 11, wherein said method is conducted at predetermined intervals on an automatic basis.

14. An apparatus for determining USDA Bostwick consistency values of a non-Newtonian fluid directly from a material production stream, the apparatus comprising:
 partial stream diverting means for diverting a partial stream from a material production stream;
 flow regulating means for regulating the flow of said fluid in the partial stream and adapted for achieving a predetermined pressure drop in said partial stream;
 weight flowrate measuring means for measuring the weight flowrate of said fluid at said predetermined pressure drop;
 temperature measuring means for measuring the temperature of said fluid in said partial stream of said fluid, and for generating a predetermined correction factor to be applied to the measured weight flowrate when the measured temperature differs from predetermined values;
 soluble solids measuring means for measuring the amount of soluble solids of said fluid stream and for making a correction on the measured weight flowrate by a predetermined factor when the measured amount of soluble solids differs from a predetermined solids value; and correlating means associated with said flow regulating means, weight flowrate measuring means, soluble solids measuring means, and temperature measuring means for receiving the respective measured values therefrom and for correlating said measured values in a predetermined functional relationship to obtain the USDA Bostwick consistency value of the fluid flowing in said stream.

15. A method of measuring USDA Bostwick value consistency of a continuous production stream of a tomato paste comprising the steps of:

establishing and maintaining a stream of said tomato paste; diverting a partial stream of said paste into a second stream thereof; regulating the flow of said paste in the second stream to achieve a predetermined pressure drop; measuring the temperature of the partial stream and making a correction on the measured weight flowrate by a predetermined factor when the measured temperature differs from a predetermined temperature value; and correlating, in a predetermined functional relationship the said measured weight flow rate, to obtain the USDA Bostwick consistency value of the paste flowing in said established stream, said correlation being conducted with said predetermined pressure drop at 30 psi/ft with the partial stream conducted through a $\frac{1}{4}''$ diameter tube of about 2 feet in length, at a temperature of 83° F., and having an amount of solids corresponding to a value of 31.6 °Brix, and wherein the USDA Bostwick consistency value is determined from the measured weight flowrate in accordance with a functional relationship of $$y = 5.48 + 4.77 \log r$$

wherein y is equal to the predicted USDA Bostwick consistency value and r is the measured weight flowrate with the correction factor applied.

* * * * *